United States Patent
Guadagno et al.

(10) Patent No.: US 10,401,370 B2
(45) Date of Patent: Sep. 3, 2019

(54) LP(A) SUBFORM SIZE IDENTIFICATION USING ELISA

(71) Applicant: True Health IP LLC, Frisco, TX (US)

(72) Inventors: Philip Guadagno, Vashon Island, WA (US); Erin Grace Summers Bellin, Sandston, VA (US); Daniel M. Hoefner, Ashland, VA (US); Mohmed Ashmaig, Glen Allen, VA (US)

(73) Assignee: True Health IP LLC, Frisco, TX (US)

( * ) Notice: Subject to any disclaimer, the term of this patent is extended or adjusted under 35 U.S.C. 154(b) by 566 days.

(21) Appl. No.: 14/924,470

(22) Filed: Oct. 27, 2015

(65) Prior Publication Data

US 2016/0116493 A1    Apr. 28, 2016

Related U.S. Application Data

(60) Provisional application No. 62/068,854, filed on Oct. 27, 2014, provisional application No. 62/147,666, filed on Apr. 15, 2015.

(51) Int. Cl.

| | |
|---|---|
| *G01N 33/92* | (2006.01) |
| *A61K 31/4535* | (2006.01) |
| *A61K 31/235* | (2006.01) |
| *A61K 31/455* | (2006.01) |
| *A61K 31/566* | (2006.01) |
| *A61K 31/397* | (2006.01) |
| *G16H 50/30* | (2018.01) |
| *G06F 19/00* | (2018.01) |

(52) U.S. Cl.
CPC ........... *G01N 33/92* (2013.01); *A61K 31/235* (2013.01); *A61K 31/397* (2013.01); *A61K 31/455* (2013.01); *A61K 31/4535* (2013.01); *A61K 31/566* (2013.01); *G06F 19/00* (2013.01); *G16H 50/30* (2018.01); *G01N 2333/775* (2013.01); *G01N 2800/044* (2013.01); *G01N 2800/32* (2013.01); *Y02A 90/26* (2018.01)

(58) Field of Classification Search
None
See application file for complete search history.

(56) References Cited

U.S. PATENT DOCUMENTS

2016/0116494 A1* 4/2016 Guadagno .............. G01N 33/92
506/9

FOREIGN PATENT DOCUMENTS

WO    WO 99/36784    7/1999

OTHER PUBLICATIONS

McConnell et al., Lipoprotein(a) mass: A massively misunderstood metric, Journal of Clinical Lipidology, 8, (2014), p. 550-553 (Year: 2104).*
Yamada et al., A new Lp(a) assay that is unaffected by apo(a) size polymorphisms, Clinica Chimica Acta, (1999), 287, p. 29-43. (Year: 1999).*
Marcovina et al., "Effect of the Number of Apolipoprotein(a) Kringle 4 Domains on Immunochemical Measurements of Lipoprotein(a)," Clinical Chemistry (1995) vol. 41, No. 2 pp. 246-255.

* cited by examiner

*Primary Examiner* — Bao Thuy L Nguyen
*Assistant Examiner* — Ellen J Marcsisin
(74) *Attorney, Agent, or Firm* — Perkins Coie LLP

(57) ABSTRACT

The application describes methods for determining the particle number and/or molar mass of lipoprotein(a) subform(s) in a biological sample using enzyme linked immunosorbent assay (ELISA). The methods described herein significantly improve lipoprotein ELISA methods and devices capable of quantifying particle numbers and population mass of Lp(a) particles. This technology offers a method for the efficient and cost-effective measurement of specific Lp(a) in a rapid, low-cost format, rather than limited measurement of Lp(a) concentration in patient tissues. The ability to measure the particle number and/or molar mass of lipoprotein(a) subform(s) in a biological sample also provides a useful diagnostic tool for assessing cardiovascular risk in a subject.

10 Claims, No Drawings

LP(A) SUBFORM SIZE IDENTIFICATION USING ELISA

The application claims the benefit of U.S. Provisional Patent Application Ser. No. 62/068,854, filed Oct. 27, 2014, and U.S. Provisional Patent Application Ser. No. 62/147,666, filed Apr. 15, 2015, which are hereby incorporated by reference in their entirety.

FIELD OF THE INVENTION

The present invention relates to methods for determining particle number and molar mass of lipoprotein(a) subform(s) in a biological sample. The invention also teaches a method of assessing cardiovascular risk in a subject.

BACKGROUND

Advances in understanding of the physiological nature of individual lipoprotein types and the effects on human health make it imperative to understand populations of lipoprotein particles and subforms, each of which is the result of, and participates in, specific metabolic processes. Such processes may be good or bad for a particular patient's health, having consequences for therapeutic efforts, including pharmacological therapy, lifestyle changes, diet changes, or other medical intervention.

Lipoproteins are particles in the blood comprising a lipid particle and a variety of apolipoprotein moieties. Lipoproteins span a wide variety of sizes and apolipoprotein content, each species having a unique metabolic pathway and unique relevance to patient health.

Lipoprotein(a) (Lp(a)) levels in a patient are known to correlate strongly with cardiovascular and metabolic health in a patient. It is a goal of existing Lp(a) assays to determine concentration of Lp(a), described as particle number (PN) and generally expressed in nmol/L from a patient's bodily fluid sample, particularly from blood, serum or plasma. The levels of Lp(a) are generally stratified into risk classifications to determine a patient's health status, trends in health status, whether treatment is necessary, and to monitor treatment.

Additionally, the determination of apolipoprotein content in a patient is known to be useful in determining overall health and for guiding treatment. For example, ApoB is known to be a risk factor of atherosclerosis independent of the lipoproteins to which it is linked. Apo(a) is another such protein with individual characteristics having significance for cardiovascular disease. Apo(a) partly comprises the Lp(a) particle and has a variety of subforms. Apo(a) subforms are derived specifically from the different possible repeated domains. It is composed of five domains called kringles (kringle I-V). Kringle IV type 2 is a repeating structure with from 3 to >50 times on a single Apo(a) molecule. The number of repeats thought to exist is variable in literature. However, kringle IV is itself comprises 10 different sequence/structures that can be recognized. Kringle IV type 2 ($KIV_2$) is the one that repeats. The number of $KIV_2$ repeats gives a molar mass of the total protein anywhere from 200 k Da to 800 k Da. The weight of the apo(a) protein translates to variation in the Lp(a) lipoprotein, which is composed of the lipid particle, one apolipoprotein B (apoB) protein and one apo(a) protein.

Although recent improvements in quantifying particle numbers of the various lipoprotein particles, particularly Lp(a), have been made (see, e.g., Marcovina et al., "Effect on the Number of Apolipoprotein(a) Kringle 4 Domains on Immunochemical Measurements of Lipoprotein(a)," *Clin. Chem.* 41(2): 246-255 (1995); Marcovina et al., "Identification of 34 Apolipoprotein(a) Subforms: Differential Expression of Apolipoprotein(a) Alleles Between American Blacks and Whites," *Biochem Biophys Res Commun* 191: 1192-6 (1993); Lackner et al., "Molecular Basis of Apolipoprotein(a) Subform Size Heterogeneity as Revealed by Pulsed-Field Gel Electrophoresis," *J Clin Invest* 87:2153-61 (1991); Kraft et al., "Apolipoprotein(a) Kringle IV Repeat Number Predicts Risk for Coronary Heart Disease," *Arterioscler Thromb Vasc Biol.* 16(6):713-9 (1996)), particle numbers are only one factor in the health effects of Lp(a). It has been determined that the Lp(a) mass is also a factor. In particular, the number of apo(a) $KIV_2$ domains has been found to contribute to an over counting of Lp(a) particles in a sample (see Id.).

Existing assays such as the Denka Seiken Lp(a)-latex assay, based on the Markovina work have been designed to measure the Lp(a) concentration (particle number) via immunological detection to minimize the kringle repeat size problem. This method, however, may be subject to interference by the variable number of apo(a) $KIV_2$ repeats, as it uses one antibody directed to the variable size $KIV_2$ domain.

Improvements are needed to permit efficient and cost-effective identification of Lp(a) subforms. Existing immunological methods are drawn only to the measurement of particle number and have no consideration of the Lp(a) mass. A full characterization would involve at least two assays to generate a complete measurement of Lp(a) measurement: first an apo(a) protein mass assay and second a molecular weight determination of the subform by amino acid analyzer or gradient gel electrophoresis.

This present invention is directed to an efficient single assay that can be used to determine Lp(a) mass and particle number, curing deficiencies in the art.

SUMMARY

The methods described herein significantly improve lipoprotein ELISA methods and devices capable of quantifying particle numbers and population mass of Lp(a) particles. This technology offers a method for the efficient and cost-effective measurement of specific Lp(a) in a rapid, low-cost format, rather than limited measurement of Lp(a) concentration in patient tissues. Moreover, the methods of the present invention do not require sample pre-treatment (e.g., denaturation or reduction), sample electrophoresis, or amino acid analysis to characterize a subject's Lp(a) content.

A first aspect of the invention relates to a method for simultaneously determining particle number and molar mass of lipoprotein(a) subform(s) (Lp(a)-P) in a biological sample. The method involves (a) providing a solid phase support with a first antibody immobilized on the support, where the first antibody is an anti-Lp(a)-capture antibody specific to a region of lipoprotein(a) other than a Kringle IV type 2 ("$KIV_2$") domain; (b) contacting the solid phase support with a biological sample comprising Lp(a)-P to permit binding of the Lp(a)-P to the first antibody; (c) contacting the solid phase support with second and third antibodies, each bound to signal-producing molecules that are distinguishable from each other, wherein the second antibody is an anti-$KIV_2$ antibody and the third antibody is an anti-apolipoprotein B (anti-apoB) antibody or an anti-apo(a) antibody specific to a region of apo(a) other than a $KIV_2$ domain; (d) detecting signals produced by the second and third antibodies; (e) quantifying, based on said detecting, the concentration of $KIV_2$ domains and apoB, respectively; and (f) determining (i) the particle number of the Lp(a)-P present in the sample based on said quantifying of the concentration of apoB and (ii) the molar mass of the Lp(a)-P present in the sample based on said quantifying of the concentration of apoB and $KIV_2$ domains.

A second aspect of the invention relates to a method of assessing cardiovascular risk in a subject. The method involves simultaneously determining particle number and molar mass of Lipoprotein(a) subform(s) (Lp(a)-P) in a biological sample from the subject, where said determining comprises quantifying apolipoprotein (a) (apo(a)), apoB, and/or a domain thereof in said Lp(a)-P by an enzyme-linked immunoassay. The method further involves assessing the cardiovascular risk of the subject based on the particle number and molar mass of the Lp(a)-P.

DETAILED DESCRIPTION

The methods described herein significantly improve upon the existing ELISA lipoprotein detection methods available for quantifying particle numbers and population mass of Lp(a) particles. The disclosed methods also provide for the efficient and cost-effective measurement of specific Lp(a) particles in a rapid, low-cost format.

The terms "lipoprotein particle," "lipid protein particle," "lipid particle," and the like as used herein refers to a particle that contains both protein and lipid. Examples of lipoprotein particles are described in more detail below.

The term "lipoprotein particle number", "particle number", and the like as used herein refers to the molar concentration, nmol/L, of lipoprotein particles present in the bodily fluid.

The term "molecular weight" may refer to molar mass.

The term "particle size" may further refer to the detected average molecular mass of population. Given the atherogenic differences associated with large and small Lp(a), an algorithm could be established for cardiovascular risk relative to Lp(a) particle number mitigated by subform size.

The term "apolipoprotein" as used herein refers to a protein that combines with lipids to form a lipoprotein particle. Examples of apolipoprotein types are described in more detail below. The unique nature of the apolipoprotein is their stoichiometric relationship to lipoprotein particles, providing an estimate of the lipoprotein particle number, which is described in more detail below.

As used herein, the term "antibody" is meant to include intact immunoglobulins derived from natural sources or from recombinant sources, as well as immunoreactive portions (i.e. antigen binding portions) of intact immunoglobulins. The antibodies of the invention may exist in a variety of forms including, for example, polyclonal antibodies, monoclonal antibodies, intracellular antibodies, antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," Proc Natl Acad Sci USA 85:5879-5883 (1988); Bird et al, "Single-Chain Antigen-Binding Proteins," *Science* 242:423-426 (1988), which are hereby incorporated by reference in their entirety).

The term "Mab" refers to a monoclonal antibody, and the term "PAb" refers to a polyclonal antibody.

The term "reference range" and like terms refer to concentrations of components of biological samples known in the art to reflect typical normal observed ranges in a population of individuals.

One aspect of the invention relates to a method for simultaneously determining particle number and molar mass of lipoprotein(a) subform(s) (Lp(a)-P) in a biological sample. The method involves (a) providing a solid phase support with a first antibody immobilized on the support, where the first antibody is an anti-Lp(a)-capture antibody specific to a region of lipoprotein(a) other than a Kringle IV type 2 ("$KIV_2$") domain; (b) contacting the solid phase support with a biological sample comprising Lp(a)-P to permit binding of the Lp(a)-P to the first antibody; (c) contacting the solid phase support with second and third antibodies, each bound to signal-producing molecules that are distinguishable from each other, wherein the second antibody is an anti-$KIV_2$ antibody and the third antibody is an anti-apolipoprotein B (anti-apoB) antibody or an anti-apo(a) antibody specific to a region of apo(a) other than a $KIV_2$ domain; (d) detecting signals produced by the second and third antibodies; (e) quantifying, based on said detecting, the concentration of $KIV_2$ domains and apoB, respectively; and (f) determining (i) the particle number of the Lp(a)-P present in the sample based on said quantifying of the concentration of apoB and (ii) the molar mass of the Lp(a)-P present in the sample based on said quantifying of the concentration of apoB and $KIV_2$ domains.

As described above, an Lp(a) particle comprises a single apo(a) protein and a single apoB protein. Apo(a) may comprise a range of sizes due to the repeats of a particular sequence of amino acids in the protein, a region described as having kringle repeats (see Lackner et al., "Molecular Basis of Apolipoprotein(a) Subform Size Heterogeneity as Revealed by Pulsed-Field Gel Electrophoresis," J Clin Invest 87:2153-61 (1991); Lackner et al., "Molecular Definition of The Extreme Size Polymorphism in Apolipoprotein (a)," Hum Mol Genet 2:933-940 (1993), each of which is hereby incorporated by reference in their entirety).

Suitable biological samples or biosamples according to the invention include human biological matrices, plasma, serum, and human lipoprotein fractions. For example, the sample may be fresh blood or stored blood or blood fractions. The sample may be a blood sample expressly obtained for the assays of this invention or a blood sample obtained for another purpose which can be subsampled for use in accordance with the methods known in the art. For instance, the biological sample may be whole blood. Whole blood may be obtained from the subject using standard clinical procedures. The biological sample may also be plasma. Plasma may be obtained from whole blood samples by centrifugation of anti-coagulated blood. The biological sample may also be serum. The sample may be pretreated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological to alkaline pH can be used.

Additional exemplary biological samples include, without limitation, urine, plasma, blood components, synovial fluid, ascitic fluid, and human lipoprotein fractions. The lipid fraction may be substantially pure such that it comprises a single lipoprotein class or subclass. An exemplary lipoprotein fraction is an Lp(a) lipoprotein fraction. Alternatively, the lipid fraction may be unpurified and comprise one or more lipoprotein particle classes or subclasses.

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Procedures for raising polyclonal antibodies are also well known (Ed Harlow and David Lane, USING ANTIBODIES: A LABORATORY MANUAL (Cold Spring Harbor Laboratory Press, 1988), which is hereby incorporated by reference in its entirety).

For example, polyclonal antibodies may be produced by injecting a suitable animal host, such as a rabbit, with the lipoprotein of interest and an adjuvant. Approximately 0.02 milliliters may be injected, with reinjection occurring every 21 days until peak antibody titer is achieved. Antibody titer may be tested by, for example, an ear bleed. Antibodies to Apo B-100 or other apolipoprotein may be produced in this manner. Alternatively, antibodies to Apo B-100 or other apolipoprotein may be purchased commercially.

In addition to whole antibodies, the invention encompasses binding portions of such antibodies. Such binding portions include the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

The first antibody may be a monoclonal antibody. Alternatively, a polyclonal antibody (PAb) may be used for antigen capture.

Solid phase supports are known to those of skill in the art. An exemplary solid phase support is a microtiter plate well.

The first antibody may be immobilized on the solid phase support via a variety of standard protocols familiar to those skilled in the art (see, e.g., US Patent Application Publication No. 20120309030, which is hereby incorporated by reference in its entirety). The solid phase support comprising an immobilized capture antibody may be used immediately or alternatively, is stored for future use as needed.

A defined volume of sample to be tested for Lp(a)-P and apo(a) subform size may be contacted with the first antibody. Standard incubation and wash steps are known in the art to perform the initial capture of the Lp(a) antigen.

In some embodiments, the method further comprises washing unbound material from the solid phase support after the solid phase support has been contacted with the biological sample. Standard washing/draining protocols may be used to remove unbound non-Lp(a) particles leaving behind only Lp(a) particles in the well.

The second contacting step involves contacting the solid phase support with second and third antibodies each bound to signal-producing molecules that are distinguishable from each other.

Suitable signal-producing molecules that are capable of producing or causing production of a detectable signal will be known to those of skill in the art. The detectable signal includes any signal suitable for detection and/or measurement by radiometric, colorimetric, fluorometric or other means known in the art.

Examples of signal-producing molecules that are capable of producing or causing production of a detectable signal include various enzymes, prosthetic groups, fluorescent materials, luminescent materials, bioluminescent materials, radioactive materials, positron emitting metals, and nonradioactive paramagnetic metal ions.

The signal-producing molecules may be coupled or conjugated either directly to the antibody or indirectly, through an intermediate (such as, for example, a linker known in the art) using techniques known in the art (see, e.g., U.S. Pat. No. 4,741,900, which is hereby incorporated by reference in its entirety).

Further examples include, but are not limited to, various enzymes. Examples of enzymes include, but are not limited to, horseradish peroxidase, alkaline phosphatase, beta-galactosidase, or acetylcholinesterase; prosthetic group complexes such as, but not limited to, streptavidin/biotin and avidin/biotin.

Examples of fluorescent materials include, but are not limited to, umbelliferone, fluorescein, fluorescein isothiocyanate, rhodamine, dichlorotriazinylamine fluorescein, dansyl chloride or phycoerythrin. Additional suitable fluorescent materials may be chosen from the group including, but not limited to, Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, Cy®3, Cy®5, Fluorescein (FITC), Oregon Green®, Pacific Blue™, Pacific Green™, Pacific Orange™, Tetramethylrhodamine (TRITC), Texas Red®, and Texas Red®.

Examples of luminescent material include, but are not limited to, luminol.

Examples of bioluminescent materials include, but not limited to, luciferase, luciferin, and aequorin.

Examples of radioactive material include, but are not limited to, bismuth (213Bi), carbon (14C), chromium (51Cr), (153Gd, 159Gd)5 gallium (68Ga, 67Ga), germanium (68Ge), holmium (166Ho), indium (115In, 113In, 112In, 111In), iodine (131I, 125I, 123I, 121I), lanthanium (140La), lutetium (177Lu), manganese (54Mn), molybdenum (99Mo), palladium (103Pd), phosphorous (32P), praseodymium (142Pr), promethium (149Pm), rhenium (186Re, 188Re), rhodium (105Rh), ruthemium (97Ru), samarium (153Sm), scandium (47Sc), selenium (75Se), strontium (85Sr), sulfur (35S), technetium (99Tc), thallium (201Ti), tin (113Sn, 117Sn), tritium (3H), xenon (133Xe), ytterbium (169Yb, 175Yb), yttrium (90Y), zinc (65Zn). Further examples include positron emitting metals using various positron emission tomographies, and nonradioactive paramagnetic metal ions.

The second antibody may be a first detection Mab (MAb') conjugated to a fluorescence reporter, specific for an apo(a) $KIV_2$ domain but not competitive with the first antibody. In one embodiment, the fluorescent reporter may be an alexa/dylite fluorescent molecule. Preferably, the fluorescent molecule is a fluorescein derivative. The signal produced by the second antibody may be proportional to the number of $KIV_2$ repeats in the captured Lp(a) particle.

The third antibody may be a second detection Mab (MAb") conjugated to a fluorescence reporter with spectral qualities separate and distinct from those of the MAb'. In one embodiment, the distinct spectral qualities of MAb" are due to a fluorescein derivative label with different excitation and emission properties than the first detection MAb'. In another embodiment, a third detection antibody may be a PAb that recognizes an epitope of apoB100. Alternatively, a third detection antibody may recognize an apo(a) domain epitopes unique to apo(a) exclusively but not KIV$_2$ nor competitive with the first antibody. The signal produced by the third antibody may be proportional to the number of Lp(a) particles captured by the first antibody.

As noted above, each detectable signal of the at least two lipoprotein-binding complexes is distinguishable from the other detectable signal. This permits cocktailing at least two lipoprotein-binding complexes where each of the complexes detects a different epitope of the Lp(a) particle, each complex also producing or capable of producing a different detectable signal. For example, a first lipoprotein-binding complex may include fluorescein isothiocyanate (FITC)-labeled antibody which binds a kringle IV repeats on the apo(a) for all Lp(a) components in a sample. A second non-kringle IV-binding complex may include rhodamine-labeled antibody which binds a second portion of apo(a). The first and second complexes may be mixed or cocktailed together. This permits probing of multiple antigenic portions of apolipoproteins in an ELISA assay. The ratios of intensities from the kringle IV repeats to non-kringle IV components of apo(a) will facilitate a more accurate measurement of Lp(a) subform size, when compared to a known kringle IV/non-kringle IV standard.

For example, the signal producing molecules may include fluorescent tags. Fluorescence tagging and the detection of natural fluorescence in molecules is a method of analytical chemistry and biology that is well known in the art. The instruments used to detect fluorescence may include the following components. A light source with a broad optical bandwidth such as a light bulb or a laser is used as the source of the stimulating light. An optical filter is used to select the light at the desired stimulation wavelength and beam it onto the sample. Optical filters are available at essentially any wavelength and are typically constructed by the deposition of layers of thin film at a fraction of the wavelength of the desired transmission wavelength. The light that exits the optical filter is then applied to the sample to stimulate the fluorescent molecule.

The molecule then emits light at its characteristic fluorescent wavelength. This light is collected by a suitable lens and is then passed through a second optical filter centered at the characteristic wavelength before being brought to a detection device such as a photomultiplier tube, a photoconductive cell, or a semiconductor optical detector. Therefore, only light at the desired characteristic wavelength is detected to determine the presence of the fluorescent molecule. Accordingly, the at least two lipoprotein-binding complexes may include fluorescent molecules that emit light at different, distinguishable fluorescent wavelengths.

As described in more detail herein, detecting signals produced by the second and third antibodies may comprise the addition of a reagent capable of interacting with the signal-producing molecule, where the signal-producing molecule produces a detectable signal upon contact with the reagent. For example, light is emitted when luciferase acts on the appropriate luciferin substrate. A secondary antibody that is coupled to a detectable signal or moiety, such as for example, an enzyme (e.g., luciferase), fluorophore, or chromophore may also be used.

The system and methods may also include a device or use of a device for detecting the detectable signal, where the detecting indicates the level of the specific Lp(a) particles or particle components in the biological sample. The device may also quantitate the level of specific Lp(a) particles or particle components based on the detection of the signal producing molecule.

The system and methods of the present invention may also include a device or use of a device for generated a report that includes, among other things, the results of lipoprotein analyses.

The presence of the detected particle or a portion thereof in reaction vessel may then be quantified by measurement of the detectable signal or moiety. The particle number may then be calculated according to known stoichiometric relationships such as the known 1:1 stoichiometry of apoB to Lp(a) or apo(a) to Lp(a). The particle number may be quantified by comparison with a separate analysis that characterizes the total lipid particle or class of lipid particle concentration in the sample. Such separate analysis may be ultracentrifugation, NMR, or any other analysis method that can characterize a concentration or total particle number for particles in the sample. Said sample used in lipid particle electrophoresis and lipid particle quantification may be different aliquots of the same sample.

A standard/calibrator with known Lp(a)-P and subform size may be included as reference for all unknown samples for which Lp(a)-P and apo(a) subform analysis is to be performed. The calibrator has a known concentration and apo(a) size. The calibrator may be a signal-producing calibrator lipoprotein.

In one embodiment, the contacting (b) further comprises contacting the solid phase support with a known concentration of a signal-producing calibrator lipoprotein comprising a known number of kringle KIV$_2$ domains, said detecting (d) further comprises detecting a signal produced by the signal-producing calibrator lipoprotein, and said determining the molar mass of the Lp(a)-P present in the sample (f)(ii) further comprises comparing the signal produced by the signal-producing calibrator lipoprotein to the detected signal from the second or third antibody. In accordance with this embodiment, the signal produced by the signal-producing calibrator lipoprotein is distinguishable from the signals produced by the second and third antibodies.

In one embodiment, the third antibody is an anti-apoB antibody.

A variety of MAbs or PAbs can be determined suitable providing they match the criteria presented above describing the antibody specification.

This technology will complement the myriad ELISA and ELISA-like protocols known in the art for execution and operation as in US Patent Application Publication No. 20120309030.

The individually measured fluorescence signals may be compared to fluorescence signals produced by the calibrator lipoprotein(a) particle, normalized to the calibrator Lp(a) particle molar concentration, and mathematically translated to the Lp(a) particle number of the sample according to the following formula:

$$[Lp(a)\text{-}P \text{ in Sample}] = ([\text{Calibrator } Lp(a)\text{-}P])\left(\frac{\text{signal produced by anti-}apoB \text{ antibody}}{\text{signal produced by calibrator}}\right)$$

where: ([Calibrator Lp(a)-P]) is the concentration of the calibrator lipoprotein in (nmol/L); (signal produced by anti-apoB antibody) is the fluorescence signal of the unknown Lp(a)-P in the sample, detected from the signal produced by the third antibody (anti-apoB antibody); and (signal produced by calibrator) is the fluorescence signal of the calibrator lipoprotein in the sample, detected from the signal produced by an anti-apoB antibody against the apoB of the calibrator lipoprotein.

The (signal produced by anti-apoB antibody) may be (signal produced by anti-apoB or anti-apo(a) non-KIV$_2$ antibody), where anti-apo(a) non-KIV$_2$ antibody is an anti-apo(a) antibody specific to a region of apo(a) other than a KIV$_2$ domain.

In some embodiments, the signal-producing calibrator lipoprotein comprises a single kringle KIV$_2$ domain.

In each of the preceding embodiments, a quantitative fluorescence imaging apparatus with optics enables the detecting of signals produced by the second and third antibodies. The imaging apparatus may further comprise a processor comprising a software algorithm to calculate concentrations of bound fluorescence reporter relative to concentrations of bound fluorescence reporters. Examples in the art include optical density calculation programs.

When the relationship between the number of KIV$_2$ repeats in an apo(a) protein of a particular Lp(a) subform is known, the total molar amount of a KIV$_2$ can be determined using the following formula:

$$\text{total mols } KIV2 = \frac{X \text{ mol } KIV2}{\text{mol } apo(a)} \times \text{total mol } apo(a)$$

Similarly, when the relationship between the number of KIV$_2$ repeats in an apo(a) protein of a calibrator Lp(a) subform is known, the total molar amount of a KIV$_2$ can be determined using the following formula:

$$\text{total mols calibrator } KIV2 = \frac{X \text{ mol calibrator } KIV2}{\text{mol calibrator } apo(a)} \times \text{total mol calibrator } apo(a)$$

As described in more detail herein, the molecular weight of an unknown or target apo(a) protein can be determined using the following formula:

$$\text{MW of } unkonwn\ apo(a) = \left(\frac{F^{unkonwn}}{F^{calibrator}}\right)\left(\frac{\text{total mol calibrator } KIV2}{\text{mol } apo(a) \text{ in } unkonwn \text{ from} Mab''}\right)(\text{MW of } KIV2) +$$

$$\text{MW of non-} KIV2\ apo(a)$$

where: $F^{unknown}$ is equivalent to the detected fluorescence of an unknown Lp(a) sample contacted with a monoclonal antibody directed to KIV type 2 repeats; $F^{calibrator}$ is equivalent to the detected fluorescence of a calibrator Lp(a) sample contacted with monoclonal antibody directed to KIV type 2 repeats; mol apo(a) in unknown from Mab" indicates that an unknown sample was contacted with a non-kringle subunit specific apo(a) antibody; MW of KIV2 indicates the molecular weight of a single KIV type 2 subunit in g/mol; and MW of non-KIV2 apo(a) indicates the molecular weight of apo(a) not due to KIV type 2 subunit repeats in grams/mol.

In any of the preceding embodiments of the methods of the present invention, the molar mass of the Lp(a)-P is determined based on molecular weight of its apo(a) according to the following formula:

$$\text{MW of Unknown } apo(a) =$$

$$\left\{ \frac{\left(\frac{F^*Unk}{F^*Cal}\right)\left(\frac{x \text{ mol } KIV_2}{\text{mol } apo(a)}\right)(\text{total mol } apo(a))}{\text{mol } apo(a) \text{ in } Unk \text{ from } MAb^*} \right\} \left(\frac{g\ KIV_2}{\text{mol } KIV_2}\right) +$$

$$\left(\frac{g \text{ non-}KIV_2}{\text{mol } apo(a)}\right)$$

where: F*Unk is the fluorescence signal of the unknown Lp(a)-P in the sample, detected from the signal produced by the second antibody (anti-KIV$_2$ antibody); F*Cal is the fluorescence signal detected from the signal-producing calibrator lipoprotein;

$$\left(\frac{x \text{ mol } KIV_2}{\text{mol } apo(a)}\right)$$

is the number of KIV-2 domain repeats per mole of apo(a) in the calibrator lipoprotein; (total mol apo(a)) is the molar concentration of apo(a) in the calibrator lipoprotein; mol apo(a) in Unk from MAb is the molar concentration of apo(a) in the unknown Lp(a)-P;

$$\left(\frac{g\ KIV_2}{\text{mol } KIV_2}\right)$$

is the molecular weight of a KIV-2 domain; and $$\left(\frac{g \text{ non-}KIV_2}{\text{mol } apo(a)}\right)$$

is the molecular weight of Lp(a) not including KIV-2 domain.

In any of the preceding embodiments of the methods of the present invention, the Lp(a)-P particle number in the sample is determined based on the following formula:

$$[Lp(a)\text{-}P \text{ in Sample}] =$$

$$([\text{Calibrator } Lp(a)\text{-}P])\left(\frac{\text{signal produced by anti-}apoB \text{ antibody}}{\text{signal produced by calibrator}}\right)$$

where ([Calibrator Lp(a)-P]) is the concentration of the calibrator lipoprotein in (nmol/L); (signal produced by anti-apoB antibody) is the fluorescence signal of the unknown Lp(a)-P in the sample, detected from the signal produced by the third antibody (anti-apoB antibody); and (signal produced by calibrator) is the fluorescence signal of the calibrator lipoprotein in the sample, detected from the signal produced by an anti-apoB antibody against the apoB of the calibrator lipoprotein.

In any of the preceding embodiments of the methods of the present invention, the third antibody is an anti-apoB antibody.

In any of the preceding embodiments of the methods of the present invention the (signal produced by anti-apoB antibody) is (signal produced by anti-apoB or anti-apo(a) non-KIV2 antibody), wherein anti-apo(a) non-KIV2 antibody is an anti-apo(a) antibody specific to a region of apo(a) other than a KIV$_2$ domain.

Results from the assay include Lp(a) particle number and Lp(a) subform population size.

The methods of the present invention can distinguish Lp(a) particles with apo(a) proteins of molecular weights, for example, greater than 700 kD, less than 600 kD, and between 600 and 700 kD. In one embodiment, the molar mass of an apo(a) protein of an individual Lp(a) subform is greater than 600 kD. In another embodiment, the molar mass of apo(a) protein of the individual Lp(a) subforms is determined to be greater than 700 kD. In an alternate embodiment, the molar mass of apo(a) protein of the individual Lp(a) subforms is between 600 and 700 kD. In a select embodiment, the molar mass of apo(a) protein of the individual Lp(a) subforms is less than 600 kD.

In accordance with this embodiment, the Lp(a)-P having apo(a) with a molecular weight less than about 600 kD are assigned to the low molar mass category, the Lp(a)-P having apo(a) with a molecular weight of between about 600 kD and 700 kD are assigned to the mid molar mass category, and the Lp(a)-P having apo(a) with a molecular weight of greater than about 700 kD are assigned to a high molar mass category.

Determining the molar mass of the population of Lp(a) subforms according to aspects illustrated herein may involve assigning the Lp(a) subform size to one of a low, mid, or high molar mass category. For instance, the Lp(a) subform size having a molar mass less than about 600 kD may be assigned to the low molar mass category; individual Lp(a) subform size having a molar mass of between about 600 kD and 700 kD may be assigned to the mid molar mass category; and individual Lp(a) subform size having a molar mass of greater than about 700 kD are assigned to a high molar mass category.

In one embodiment, the method further comprises assigning the Lp(a) subform(s) to a low, mid, or high molar mass category.

A second aspect of the invention relates to a method of assessing cardiovascular risk in a subject. The method involves simultaneously determining particle number and molar mass of Lipoprotein(a) subform(s) (Lp(a)-P) in a biological sample from the subject, where said determining comprises quantifying apolipoprotein (a) (apo(a)), apoB, and/or a domain thereof in said Lp(a)-P by an enzyme-linked immunoassay. The method further involves assessing the cardiovascular risk of the subject based on the particle number and molar mass of the Lp(a)-P.

Suitable biological samples or biosamples according to the invention include human biological matrices, plasma, serum, and human lipoprotein fractions. As described above, suitable biological samples according to the invention include, without limitation, fresh blood, stored blood, or blood fractions.

The subject may be healthy. Alternatively, the subject may be known to suffer from a cardiovascular or metabolic disorder and/or at risk of suffering from a cardiovascular or metabolic disorder. The subject may be a patient suspected of suffering from a lipoprotein-associated disorder including, but not limited to, cardiovascular disorders and obesity. Additional lipoprotein disorders include hyperlipidemia (i.e., the abnormal elevation of lipids or lipoproteins in the blood), arteriovascular disease, atherosclerosis, pancreatitis, and liver disorders. Elevated or unbalanced lipid and lipoprotein levels are reflective of a subject's development of or progression of diabetic conditions and metabolic disorders.

In one embodiment, determining the particle number and molar mass of the Lp(a)-P involves: (a) providing a solid phase support with a first antibody immobilized on the support, wherein the first antibody is an anti-Lp(a)-capture antibody specific to a region of lipoprotein(a) other than a Kringle IV type 2 ("KIV$_2$") domain; (b) contacting the solid phase support with a biological sample comprising Lp(a)-P to permit binding of the Lp(a)-P to the first antibody; (c) contacting the solid phase support with second and third antibodies, each bound to signal-producing molecules that are distinguishable from each other, where the second antibody is an anti-KIV$_2$ antibody and the third antibody is an anti-apolipoprotein B (anti-apoB) antibody or an anti-apo(a) antibody specific to a region of apo(a) other than a KIV$_2$ domain; (d) detecting signals produced by the second and third antibodies; (e) quantifying, based on said detecting, the concentration of KIV$_2$ domains and apoB, respectively; and (f) determining (i) the particle number of the Lp(a)-P present in the sample based on said quantifying of the concentration of apoB and (ii) the molar mass of the Lp(a)-P present in the sample based on said quantifying of the concentration of apoB and KIV$_2$ domains.

In accordance with this embodiment, contacting (b) further involves contacting the solid phase support with a known concentration of a signal-producing calibrator lipoprotein comprising a known number of kringle KIV$_2$ domains, detecting (d) further involves detecting a signal produced by the signal-producing calibrator lipoprotein, and determining the molar mass of the Lp(a)-P present in the sample in step (f) further involves comparing the signal produced by the signal-producing calibrator lipoprotein to the detected signal from the second or third antibody. In accordance with this aspect of the invention, the signal produced by the signal-producing calibrator lipoprotein is distinguishable from the signals produced by the first and second antibodies.

In one embodiment, the method further comprises washing unbound material from the solid phase support after the support has been contacted with the biological sample.

In another embodiment, the signal-producing calibrator lipoprotein comprises a single kringle KIV$_2$ domain.

As described above, the system and methods of the present invention may also include a device or use of a device for detecting the detectable signal, where the detecting indicates the level of the specific Lp(a) particles or particle components in the biological sample. The device may also quantitate the level of specific Lp(a) particles or particle components based on the detection of the signal producing molecule.

The presence of the detected particle or a portion thereof in reaction vessel may then be quantified by measurement of the detectable signal or moiety. The particle number may then be calculated according to known stoichiometric relationships such as the known 1:1 stoichiometry of apoB to Lp(a) or apo(a) to Lp(a). The particle number may be quantified by comparison with a separate analysis that characterizes the total lipid particle or class of lipid particle concentration in the sample. Such separate analysis may be ultracentrifugation, NMR, or any other analysis method that can characterize a concentration or total particle number for particles in the sample. Said sample used in lipid particle electrophoresis and lipid particle quantification may be different aliquots of the same sample.

In any of the preceding embodiments of the methods of the present invention, the molar mass of the Lp(a)-P is determined based on molecular weight of its apo(a) according to the following formula:

$$\text{MW of Unknown } apo(a) =$$

$$\left\{ \frac{\left(\frac{F^*Unk}{F^*Cal}\right)\left(\frac{x \text{ mol } KIV_2}{\text{mol } apo(a)}\right)(\text{total mol } apo(a))}{\text{mol } apo(a) \text{ in } Unk \text{ from } MAb^*} \right\} \left(\frac{g \ KIV_2}{\text{mol } KIV_2}\right) +$$

$$\left(\frac{g \ \text{non-}KIV_2}{\text{mol } apo(a)}\right)$$

where: F*Unk is the fluorescence signal of the unknown Lp(a)-P in the sample, detected from the signal produced by the second antibody (anti-KIV$_2$ antibody); F*Cal is the fluorescence signal detected from the signal-producing calibrator lipoprotein;

$$\left(\frac{x \text{ mol } KIV_2}{\text{mol } apo(a)}\right)$$

is the number of KIV-2 domain repeats per mole of apo(a) in the calibrator lipoprotein; (total mol apo(a)) is the molar concentration of apo(a) in the calibrator lipoprotein; mol apo(a) in Unk from MAb is the molar concentration of apo(a) in the unknown Lp(a)-P;

$$\left(\frac{g \ KIV_2}{\text{mol } KIV_2}\right)$$

is the molecular weight of a KIV-2 domain; and $$\left(\frac{g \ \text{non-}KIV_2}{\text{mol } apo(a)}\right)$$

is the molecular weight of Lp(a) not including KIV-2 domain.

In any of the preceding embodiments of the methods of the present invention, the Lp(a)-P particle number in the sample is determined based on the following formula:

$$[Lp(a)\text{-}P \text{ in Sample}] =$$

$$([\text{Calibrator } Lp(a)\text{-}P])\left(\frac{\text{signal produced by anti-}apoB \text{ antibody}}{\text{signal produced by calibrator}}\right)$$

where: ([Calibrator Lp(a)-P]) is the concentration of the calibrator lipoprotein in (nmol/L); (signal produced by anti-apoB antibody) is the fluorescence signal of the unknown Lp(a)-P in the sample, detected from the signal produced by the third antibody (anti-apoB antibody); and (signal produced by calibrator) is the fluorescence signal of the calibrator lipoprotein in the sample, detected from the signal produced by an anti-apoB antibody against the apoB of the calibrator lipoprotein.

In any of the preceding embodiments of the methods of the present invention, the third antibody is an anti-apoB antibody.

In any of the preceding embodiments of the methods of the present invention the (signal produced by anti-apoB antibody) is (signal produced by anti-apoB or anti-apo(a) non-KIV2 antibody), wherein anti-apo(a) non-KIV$_2$ antibody is an anti-apo(a) antibody specific to a region of apo(a) other than a KIV$_2$ domain.

In one embodiment, the method further comprises assigning the Lp(a)-P to a low, mid, or high molar mass category.

As described above, the method can distinguish Lp(a) particles with apo(a) proteins of molecular weights, for example, greater than 700 kD, less than 600 kD and between 600 and 700 kD. Determining the molar mass of the population of Lp(a) subforms according to aspects illustrated herein may involve assigning the Lp(a) subform size to one of a low, mid, or high molar mass category. In accordance with this embodiment of the present application, the Lp(a)-P having apo(a) with a molecular weight less than about 600 kD are assigned to the low molar mass category, the Lp(a)-P having apo(a) with a molecular weight of between about 600 kD and 700 kD are assigned to the mid molar mass category, and the Lp(a)-P having apo(a) with a molecular weight of greater than about 700 kD are assigned to a high molar mass category.

Determining cardiovascular risk according to aspects described herein may involve assigning the subject to one of a low, moderate, or high cardiovascular risk category. There are well established recommendations for cut-off values for biochemical markers for determining risk (see Rifai et al., "Apolipoprotein(a) Size and Lipoprotein(a) Concentration and Future Risk of Angina Pectoris with Evidence of Severe Coronary Atherosclerosis in Men: The Physicians' Health Study," *Clinical Chem.* 58(8):1364-1371 (2004); Erqou et al., "Apolipoprotein(a) Isoforms and the Risk of Vascular Disease," *J. Am. Coll. Cardiology* 55(19): 2160-7 (2010); and Thomas Dayspring "Lipoprotein(a)," available at lipid-center.com/pdf/Entire_Lpa_Complexities (2010); BRAUNWALD'S HEART DISEASE: A TEXTBOOK OF CARDIOVASCULAR MEDICINE 9th ed. (Bonow et al. eds. 2011); "Executive Summary of The Third Report of The National Cholesterol Education Program (NCEP) Expert Panel on Detection, Evaluation, And Treatment of High Blood Cholesterol In Adults (Adult Treatment Panel III)," *JAMA* 285:2486-2497 (2001); "Adult Treatment Panel III (ATP III) of the National Cholesterol Education Program. Implications of Recent Clinical Trials for the National Cholesterol Education Program Adult Treatment Panel III Guidelines," *Circulation* 110(2):227-39 (2004); and MedlinePlus, A service of the U.S. National Library of Medicine and National Institutes of Health available at nlm.nih.gov/medlineplus, which are hereby incorporated by reference in their entirety.)

In one embodiment, the subject is assigned to one of a low, moderate, or high cardiovascular risk categories based on the particle number and molar mass of the Lp(a)-P.

The invention also includes selecting a therapeutic regimen or modifying an existing therapeutic regimen based on the risk for cardiovascular disease determined. For instance, an individual may be determined to be at an elevated risk according to the methods and a therapeutic regimen may then be selected or modified based on the elevated risk.

The selected therapeutic regimen may include drugs or supplements. Suitable drugs or supplements include those administered for the purpose of lowering serum cholesterol, lowering LDL, IDL, and VLDL, Lp(a) and/or raising HDL, as known in the art.

In one embodiment, a therapeutic regimen for the subject is selected, or an existing therapeutic regimen for the subject is modified, based on the particle number and molar mass of the Lp(a)-P. In accordance with this embodiment, the selected therapeutic regimen comprises administering a drug and/or a supplement or the existing therapeutic regimen comprises administering a modified dose of a drug and/or a supplement. In some embodiments, the drug is selected from the group consisting of niacin, an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, an angiotensin system inhibitor, and combinations thereof. In other embodiments, the drug is selected from the group consisting of niacin, fenofibrate, estrogen, and raloxifene. In one embodiment, the drug is selected from the group consisting of niacin, ezetimibe, a statin, or a combination thereof.

The selected therapeutic regimen may also involve giving recommendations on making or maintaining lifestyle choices based on the results of said cardiovascular risk. Lifestyle choices may involve changes in diet, changes in exercise, reducing or eliminating smoking, or a combination thereof.

As described in more detail herein, a report may also be generated that includes, among other things, a description of the selected treatment regimen. In some embodiments, the results of lipoprotein analyses are reported in such a report. A report refers in the context of lipoprotein and other lipid analyses to a report provided, for example to a patient, a clinician, other health care provider, epidemiologist, and the like, which includes the results of analysis of a biological specimen, for example a plasma specimen, from an individual. Reports can be presented in printed or electronic form, or in any form convenient for analysis, review and/or archiving of the data therein, as known in the art.

A report may include identifying information about the individual subject of the report, including without limitation name, address, gender, identification information (e.g., social security number, insurance numbers), and the like. A report may include biochemical characterization of the lipids in the sample in addition to Lp(a), for example without limitation triglycerides, total cholesterol, LDL cholesterol, and/or HDL cholesterol, and the like. A report may further include characterization of lipoproteins, and reference ranges therefore, conducted on samples prepared by the methods provided herein.

As described above, the term "reference range" and like terms refer to concentrations of components of biological samples known in the art to reflect typical normal observed ranges in a population of individuals. Exemplary characterization of lipoproteins in an analysis report may include the concentration and reference range for VLDL, IDL, Lp(a), LDL and HDL, and subclasses thereof. A report may further include lipoprotein size distribution trends.

The invention also may further include administering the selected therapeutic regimen or modified therapeutic regimen to the subject. Accordingly, a further aspect of the present invention relates to a method of treating a subject having an elevated risk for cardiovascular disease determined.

The invention also relates to a method of monitoring the risk for developing cardiovascular disease. This method includes determining whether a subject is at increased risk for cardiovascular disease at a first time point and repeating the determining at one or more later time points (e.g., before and after therapeutic intervention or at progressive time points during a course of therapeutic intervention). The determined risk at each progressive time point is compared the determined risk from one or more earlier time points to evaluate whether the subject's risk for developing cardiovascular disease has increased or decreased, thereby monitoring the risk for developing cardiovascular disease. This method may involve assigning a risk category based on the determined risk for developing cardiovascular disease and comparing the risk categories assigned at progressive time points (e.g., comparing a first risk category determined at a first time point to a second risk category taken at a second time point), thereby monitoring the risk for developing cardiovascular disease.

What is claimed is:

1. A method for simultaneously determining particle number and molar mass of lipoprotein(a) subforms (Lp(a)-P) in a biological sample, wherein the lipoprotein(a) subforms comprise an apolipoprotein(a) (apo(a)) domain, the method comprising:
   (a) providing a solid phase support with a first antibody immobilized on the support, wherein the first antibody is an anti-Lp(a)-capture antibody specific to a region of lipoprotein(a) other than a Kringle IV type 2 (KIV2) domain;
   (b) contacting the solid phase support with a biological sample comprising Lp(a)-P subforms to permit binding of the Lp(a)-P subforms to the first antibody and with a known concentration of signal-producing calibrator lipoprotein comprising a known number of KIV2 domains;
   (c) contacting the solid phase support with second and third antibodies, each bound to fluorescence signal-producing molecules that are distinguishable from each other, wherein the second antibody is an anti-KIV2 antibody and the third antibody is an anti-apolipoproteinB (anti-apoB) antibody, and further wherein the signal producing calibrator lipoprotein is distinguishable from the fluorescence signal producing molecules bound to the first and second antibodies;
   (d) detecting fluorescence signals produced by the second and third antibodies and detecting signal produced by the signal producing calibrator lipoprotein;
   (e) quantifying the concentration of KIV2 domains based on the detected signal of the second antibody and quantifying the concentration of apoB based on the detected signal of the third antibody; and
   (f) determining the particle number and the molar mass of the Lp(a)-P subforms present in the sample,
   wherein (i) the particle number of the Lp(a)-P subforms present in the sample is determined by the following formula for concentration of the Lp(a)-P subforms:

$$[Lp(a)\text{-}P \text{ in sample}] = ([\text{Calibrator } Lp(a)\text{-}P]) \left( \frac{\text{signal produced by anti-}apoB \text{ antibody}}{\text{signal produced by calibrator}} \right)$$

wherein:
Calibrator Lp(a)-P is the concentration of the calibrator lipoprotein in nmol/L, signal produced by anti-apoB antibody is the fluorescence signal produced by the third antibody,
signal produced by calibrator is the fluorescence signal of the signal producing calibrator lipoprotein, and
wherein (ii) a molar mass of the Lp(a)-P present in the sample is based on the molecular weight (MW) of apo(a) present in the Lp(a) subforms determined by the following formula:

$$\text{MW of Unknown } apo(a) =$$

$$\left\{ \frac{\left(\frac{F*Unk}{F*Cal}\right)\left(\frac{x \text{ mol } KIV2}{\text{mol } apo(a)}\right)(\text{total mol } apo(a))}{\text{mol } apo(a) \text{ in Unk from Mab}} \right\} \left(\frac{g\ KIV2}{\text{mol } KIV2}\right) +$$

$$\left(\frac{g\ \text{non-}KIV2}{\text{mol } apo(a)}\right)$$

wherein:

MW of Unknown apo(a) is molecular weight of apo(a) present in the subforms,

F*Unk is the fluorescence signal produced by the second antibody,

F*Cal is the fluorescence signal of the signal producing calibrator lipoprotein, $$\frac{x \text{ mol } KIV2}{\text{mol } apo(a)}$$

is the number of KIV2 domain repeats per mole of apo(a) in the calibrator lipoprotein, total mol apo(a) is the molar concentration of apo(a) in the calibrator lipoprotein, mol apo(a) in Unk from Mab is the molar concentration of apo(a) from the Lp(a)-P subforms in the sample, $$\frac{g\ KIV2}{\text{mol } KIV2}$$

is molecular weight of a KIV2 domain, and $$\frac{g\ \text{non-}KIV2}{\text{mol } apo(a)}$$

is molecular weight or Lp(a) not including KIV2 domain.

2. The method of claim 1, wherein the method further comprises washing unbound material from the solid phase support after the solid phase support has been contacted with the biological sample.

3. The method according to claim 1, wherein the method further comprises assigning the Lp(a)-P subforms to low, mid, or high molar mass category, wherein the Lp(a)-P subforms having apo(a) with a molecular weight less than about 600 kD are assigned to the low molar mass category, the Lp(a)-P subforms having apo(a) with a molecular weight of between about 600 kD and 700 kD are assigned to the mid molar mass category, and the Lp(a)-P subforms having apo(a) with a molecular weight of greater than about 700 kD are assigned to the high molar mass category.

4. A method of assessing cardiovascular risk in a subject, comprising:
  (a) performing the method of claim 1 in order to determine a particle number and molar mass of Lp(a)-P subforms in a subject's biological sample; and
  (b) assessing the cardiovascular risk of the subject based on the particle number and the molar mass of the Lp(a)-P subforms, wherein assessing comprises assigning the subject to a risk category for predicting cardiovascular disease based on the Lp(a)-P particle number and molar mass.

5. The method of claim 4, further comprising selecting a therapeutic regimen, or modifying an existing therapeutic regimen, for the subject based on the assigned risk category.

6. The method of claim 5, wherein the therapeutic regimen comprises administering a drug and/or supplement.

7. The method of claim 6, wherein the drug is selected from the group consisting of niacin, fenofibrate, estrogen, and raloxifene.

8. The method of claim 6, wherein the drug is selected from the group consisting of niacin, ezetimibe, a statin, or a combination thereof.

9. The method of claim 5, wherein the therapeutic regimen involves giving recommendations on making or maintaining lifestyle choices.

10. The method of claim 9, wherein the lifestyle choices involve changes in diet, changes in exercise, reducing or eliminating smoking, or a combination thereof.

* * * * *